United States Patent
Farmer et al.

(10) Patent No.: US 11,969,985 B2
(45) Date of Patent: *Apr. 30, 2024

(54) METHOD OF USING A STERILIZATION WRAP SYSTEM

(71) Applicant: O&M Halyard, Inc., Mechanicsville, VA (US)

(72) Inventors: Jeffrey James Farmer, Roswell, GA (US); Kelly L. Holt, Alpharetta, GA (US); Ronald K. Anderson, Fruit Heights, UT (US); Melissa R. Gaynor, Roswell, GA (US); Corinna Schwarz, Roswell, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,320

(22) Filed: Apr. 25, 2023

(65) Prior Publication Data

US 2023/0256709 A1    Aug. 17, 2023

Related U.S. Application Data

(60) Continuation of application No. 17/405,081, filed on Aug. 18, 2021, now Pat. No. 11,654,652, which is a
(Continued)

(51) Int. Cl.
*B32B 7/023* (2019.01)
*A61B 17/00* (2006.01)
(Continued)

(52) U.S. Cl.
CPC .............. *B32B 7/023* (2019.01); *A61B 46/40* (2016.02); *A61B 50/30* (2016.02); *A61L 2/07* (2013.01);
(Continued)

(58) Field of Classification Search
CPC .. B32B 7/02; B32B 7/023; B32B 5/26; B32B 7/05; B32B 5/022; B32B 5/22;
(Continued)

(56) References Cited

U.S. PATENT DOCUMENTS 3,685,720 A   8/1972   Brady
3,761,013 A   9/1973   Schuster
(Continued)

FOREIGN PATENT DOCUMENTS

GB   1 592 214 A    7/1981
JP   S5485889 U    6/1979
(Continued)

OTHER PUBLICATIONS

English Translation of the relevant extracts of The State Standard of the USSR, No. 19088-89, "Paper and Cardboard. Terms and Revealing Defects", 1990. pp. 3-5.

*Primary Examiner* — Elizabeth M Imani
(74) *Attorney, Agent, or Firm* — Dority & Manning, P.A.

(57) ABSTRACT

A method of using a sterilization wrap system including a permeable material having barrier properties and having a first surface and a second opposing surface, the exterior panel being substantially opaque or having a first level of translucence, and an interior panel including a permeable material having barrier properties and having a first surface and a second opposing surface, the interior panel having a level of translucence that is higher than the translucence of the exterior panel, the panels being joined together over at least a portion of their surfaces. Also disclosed is inspection of the sterilization wrap system for exterior panel breaches by looking for light passing through a panel facing the viewer.

22 Claims, 9 Drawing Sheets

Related U.S. Application Data continuation of application No. 16/847,826, filed on Apr. 14, 2020, now Pat. No. 11,123,952, which is a continuation of application No. 15/623,472, filed on Jun. 15, 2017, now Pat. No. 10,730,265, which is a division of application No. 13/667,526, filed on Nov. 2, 2012, now Pat. No. 9,718,253.

(60) Provisional application No. 61/592,233, filed on Jan. 30, 2012, provisional application No. 61/557,215, filed on Nov. 8, 2011.

(51) Int. Cl.

| | | |
|---|---|---|
| *A61B 46/00* | (2016.01) | |
| *A61B 50/30* | (2016.01) | |
| *A61L 2/07* | (2006.01) | |
| *A61L 2/20* | (2006.01) | |
| *A61L 2/26* | (2006.01) | |
| *B32B 5/02* | (2006.01) | |
| *B32B 5/22* | (2006.01) | |
| *B32B 5/26* | (2006.01) | |
| *B32B 7/05* | (2019.01) | |
| *G01N 21/88* | (2006.01) | |

(52) U.S. Cl.
CPC ............... *A61L 2/206* (2013.01); *A61L 2/26* (2013.01); *B32B 5/022* (2013.01); *B32B 5/22* (2013.01); *B32B 5/26* (2013.01); *B32B 7/05* (2019.01); *G01N 21/8803* (2013.01); *A61B 2017/00907* (2013.01); *A61L 2202/181* (2013.01); *A61L 2202/24* (2013.01); *B32B 2262/0253* (2013.01); *B32B 2307/404* (2013.01); *B32B 2307/41* (2013.01); *B32B 2307/414* (2013.01); *B32B 2307/724* (2013.01); *B32B 2439/80* (2013.01)

(58) Field of Classification Search
CPC ...... B32B 2262/0253; B32B 2307/404; B32B 2307/41; B32B 2439/80; B32B 2307/414; B32B 2307/724; A61L 2/07; A61L 2/206; A61L 2/26; A61L 2202/24; A61L 2202/181; A61B 50/30; A61B 46/40; A61B 2017/00907; G01N 21/8803; G01N 21/88

See application file for complete search history.

(56) References Cited

U.S. PATENT DOCUMENTS

| | | |
|---|---|---|
| 3,990,872 A | 11/1976 | Cullen |
| 4,041,203 A | 8/1977 | Brock et al. |
| 4,516,679 A | 5/1985 | Simpson et al. |
| 5,635,134 A * | 6/1997 | Bourne ............... B32B 7/05 422/26 |
| 5,688,476 A | 11/1997 | Bourne et al. |
| 5,899,856 A | 5/1999 | Schoendorfer et al. |
| 6,809,048 B1 | 10/2004 | Jacobs |
| 2001/0036519 A1 | 11/2001 | Bayer |
| 2005/0163654 A1 | 7/2005 | Stecklein et al. |
| 2005/0170726 A1 | 8/2005 | Brunson et al. |
| 2006/0067855 A1 | 3/2006 | Mathis et al. |
| 2006/0104857 A1 | 5/2006 | Pigott et al. |
| 2007/0129696 A1 | 6/2007 | Soerens et al. |
| 2009/0053103 A1 * | 2/2009 | Mortimer ............ A61L 2/206 206/439 |
| 2012/0234333 A1 | 9/2012 | Jenkins et al. |

FOREIGN PATENT DOCUMENTS

| | | |
|---|---|---|
| JP | S54116581 U | 8/1983 |
| WO | WO 95/01135 A1 | 1/1995 |
| WO | WO 2008/083426 A1 | 7/2008 |

* cited by examiner

METHOD OF USING A STERILIZATION WRAP SYSTEM

RELATED APPLICATIONS

This application is a continuation application of U.S. patent application Ser. No. 17/405,081, filed on Aug. 18, 2021, which is a continuation application of U.S. patent application Ser. No. 16/847,826, filed on Apr. 14, 2020, which is a continuation application of U.S. patent application Ser. No. 15/623,472, filed on Jun. 15, 2017, which is a divisional application of U.S. patent application Ser. No. 13/667,526, filed on Nov. 2, 2012, which claims the benefit of priority from U.S. Provisional Application No. 61/557,215 entitled "Method of Using a Sterilization Wrap System," filed on Nov. 8, 2011, and from U.S. Provisional Application No. 61/592,233 entitled "Method of Using a Sterilization Wrap System" filed on Jan. 30, 2012, the contents of which are incorporated herein by reference.

FIELD OF THE INVENTION

The present invention relates in general to disposable wraps used to contain content to be sterilized and store that content aseptically until use.

BACKGROUND OF THE INVENTION

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are wrapped in sterilization fabric and then sterilized and stored for subsequent use. Disposable sterilization fabric is typically cut into predetermined rectangular shapes and sold as sterilization wraps.

Conventional disposable sterilization wrap is a flat, featureless sheet of material that may occasionally contain one or more additional layers of material for strength or absorbency. Such sterilization wrap is frequently made of inexpensive, relatively impermeable material such as, for example, paper and the like. The properties of these materials have generally influenced folding techniques and wrapping configurations to ensure the sterility of the wrapped tray or article.

For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. Patent Application Publication No. 2001/0036519 by Robert T. Bayer discloses a two ply sterilization wrap that is formed of a single sheet of sterilization wrap material which is folded to form two similarly sized, superposed panels that are bonded to each other. As yet another example, U.S. Patent Application Publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

There are many ways items conventionally wrapped or packaged in sterilization wraps can be contaminated. For example, certain modes of wrap failure such as knife cuts, abrasion and punctures are well-recognized. There are other modes of failure that are as common if not more common. These include pressure cuts, snag cuts and pressure holes.

A pressure cut can appear as a knife cut, but upon closer examination, the fibers around the very edge of the cut have been "welded" or stuck together. The edge of the cut may feel hard to the touch. This type of cut usually follows the perimeter or outline of the bottom of the instrument tray. It may also occur on the top of the instrument tray, if a number of trays have been stacked upon one another. An example of a typical event that may generate a pressure cut would be lifting the front end of a 20 pound tray so that all the weight of the tray is resting on a back edge, and pulling it across the storage shelf before lifting. This is similar to cutting the wrap with scissors; the material is caught between two layers of hard solid interfaces with a shearing action applied to the material.

In a snag cut, the edges of the cut show loose fibers hanging and/or there are individual fibers spanning across the width of the cut. The edges of the cut are not rough or hard, as with the pressure cut. In larger snag cuts, the shape of the cut area resembles a triangle, with the point of the triangle being where the snag began. The snag cut will occur along the edges of the wrapped instrument tray if the tray is very loosely wrapped. Otherwise, this type of cut will occur on the other areas of the tray where the wrap is too loose and can be caught by rough surfaces or corners. This type of cut is generally due to the tray being pulled or dragged across a roughened surface, often an older, well-used sterilizer cart. This cut can also occur when a loosely wrapped area of a tray gets caught on the corners or edges of objects.

A pressure hole may appear to be a tiny opening where the fibers around the very edge of the hole have been "welded" or stuck together. This type of hole is usually found along the perimeter of the bottom of an instrument tray. It may also occur on the top of the instrument tray if a number of trays have been stacked upon it. An example of a typical event that may generate a pressure hole would be a tray being dropped (even a small distance) onto an edge of a cart or storage shelf while being transported to different areas of the hospital.

During typical practice, the sterilization wrap is inspected for holes, tears or other breaches after it is removed from the sterilized article. It has been proposed in International Publication No. WO 2008/083426 A1 "Sterilization Wrapping System" by Spierenburg, that having color differences between superposed layers of a sterilization wrap system could make detection of breaches easier because a viewer looking directly at a breach will notice the contrast between the color of the material around the breach and the material exposed by the breach. However, such a system fails to address the problem of detecting breaches in the sheet of a multi-layer sterilization wrap on the opposite side of the viewer such that the viewer cannot look directly at the breach to see the difference in color.

Accordingly, there is an unmet need for an easy method to inspect a sterilization assembly, package or system that simplifies the task of identifying a breach—particular a breach in a multi-layer sterilization wrap system that is on the opposite side of a viewer.

BRIEF SUMMARY OF THE INVENTION

The problems described above are addressed by the present invention which encompasses a method of using a sterilization wrap system. The method includes the steps of providing an article and then wrapping the article with a sterilization wrap system having an exterior panel including a permeable material having barrier properties and having a first surface and a second opposing surface, the exterior panel being substantially opaque or having a first level of translucence; and an interior panel including a gas permeable material having barrier properties and having a first surface and a second opposing surface, the interior panel having a level of translucence that is higher than the translucence of the exterior panel, the panels being joined together over at least a portion of their surfaces. The method further includes the steps of exposing the wrapped article to sterilizing conditions for a sufficient time such that the article is sterilized; unwrapping the article and removing the sterilization wrap system; positioning the sterilization wrap system so at least a portion of the exterior panel of the sterilization wrap system is opposite a viewer and a corresponding portion of the interior panel is facing a viewer; and inspecting the sterilization wrap system for exterior panel breaches by looking for light passing through the interior panel facing the viewer.

The sterilization wrap system is desirably positioned so that the sterilization wrap system is located between a light source and a viewer. In an aspect of the invention, the sterilization wrap system may be positioned so that the first panel and the second panel are separated by a space in a portion of the sterilization wrap system being inspected.

According to the invention, the second panel includes a plurality of bond points and the bond points define discrete locations having higher translucence than locations on the permeable material of the second panel that are not bond points such that inspecting the sterilization wrap system for exterior panel breaches is carried out by looking for light passing through a panel facing the viewer by way of one or more bond points.

The present invention also encompasses a method of inspecting a sterilization wrap system after it is removed from an article. The method includes the steps of: positioning a sterilization wrap system with respect to a viewer (that is, a sterilization wrap system including a first panel composed of a gas permeable material having barrier properties and having a first surface and a second opposing surface, the first panel being substantially opaque or having a first level of translucence; and a second panel composed of a permeable material having barrier properties and having a first surface and a second opposing surface, the second panel having a level of translucence that is higher than the translucence of the first panel, wherein the panels are joined together over at least a portion of their surfaces and wherein at least a portion of one panel of the sterilization wrap system is opposite a viewer and a corresponding portion of the other panel is facing a viewer); and inspecting the sterilization wrap system for breaches in the panel opposite the viewer by looking for light passing through the panel facing the viewer.

The sterilization wrap system is desirably positioned so that the sterilization wrap system is located between a light source and a viewer. In an aspect of the invention, the sterilization wrap system may be positioned so that the first panel and the second panel are separated by a space in a portion of the sterilization wrap system being inspected.

According to another aspect of the invention, the first panel, the second panel or both panels may include a plurality of bond points and the bond points define discrete locations having higher translucence than locations on the permeable material of the respective first or second panel that are not bond points such that inspecting the sterilization wrap system for breaches in the panel opposite the viewer is carried out by looking for light passing through the panel facing the viewer by way of one or more bond points. According to the invention, the first panel may be opposite the viewer and the second panel may be facing the viewer. Alternatively, the first panel may be facing the viewer and the second panel may be opposite the viewer.

The present invention also encompasses a sterilization wrap system that includes: a first panel having a permeable material having barrier properties and having a first surface and a second opposing surface, the first panel being substantially opaque or having a first level of translucence; and a second panel including a permeable material having barrier properties and having a first surface and a second opposing surface, the second panel having a level of translucence that is higher than the translucence of the first panel, the panels being joined together over at least a portion of their surfaces.

The second panel may include a plurality of bond points. These bond points define discrete locations having higher translucence than locations on the permeable material of the second panel that are not bond points. For example, the plurality of bond points on the second panel may provide the second panel with at least 15 percent higher translucence than locations on the permeable material of the second panel that are not bond points. As another example, the plurality of bond points on the second panel may provide the second panel with at least 30 percent higher translucence. As yet another example, plurality of bond points on the second panel may provide the second panel with at least 45 percent higher translucence.

In an aspect of the invention, the permeable material of the second panel may be a permeable material that has a higher level of translucence than the permeable material of the first panel. For example, the difference in translucence between first panel and the second panel may be at least 15 percent. As another example, the difference in translucence between first panel and the second panel may be at least 30 percent. As yet another example, the difference in translucence between first panel and the second panel may be at least 45 percent.

Desirably, the sterilization system is adapted for use in steam sterilizing conditions, ethylene oxide sterilizing conditions, as well as other conventional sterilizing systems.

According to an aspect of the invention, the first panel and the second panel may be a single sheet of permeable material having barrier properties, the single sheet being folded to form a first panel and second panel and at least the edges opposite the fold being joined together. In another aspect of the invention, the first panel and the second panel may be independent sheets of material that are joined together. For example, the first panel and second panel may each have a periphery and the first panel and second panel may be overlaid and joined at the periphery. Desirably, at least one of the permeable materials having barrier properties is a spunbond/meltblown/spunbond (SMS) material.

The present invention also encompasses a sterilization wrap system composed of a permeable material having barrier properties and the permeable material includes: a first sheet having a first surface and a second opposing surface, the first material being substantially opaque or having a first level of translucence; and a second sheet having a first surface and a second opposing surface, the second sheet having a level of translucence that is higher than the translucence of the first sheet, the sheets being joined together over at least a portion of their surfaces.

The second sheet may include a plurality of bond points such that the bond points define discrete locations having higher translucence than locations on the second sheet that are not bond points. For example, the plurality of bond points on the second sheet may provide the second sheet with at least 15 percent higher translucence than locations on the second sheet that are not bond points. As another example, the plurality of bond points on the second sheet may provide the second sheet with at least 30 percent higher translucence. As yet another example, the plurality of bond points on the second sheet may provide the second sheet with at least 45 percent higher translucence.

In an aspect of the invention, the first sheet may be made of a first permeable material and the second sheet may be made of a second permeable material that has a higher level of translucence than the first material. For example, the difference in translucence between first sheet and the second sheet may be at least 15 percent. As another example, the difference in translucence between first sheet and the second sheet may be at least 30 percent. As yet another example, the difference in translucence between first sheet and the second sheet may be at least 45 percent.

In an aspect of the invention, the first sheet and the second sheet may be a single sheet of permeable material having barrier properties, the single sheet being folded over to form a first sheet and second sheet and at least the edges opposite the fold being joined together. In another aspect of the invention, the first sheet and the second sheet may be independent sheets of material that are joined together. For example, the first sheet and second sheet may each have a periphery and the first sheet and second sheet may be overlaid and joined at the periphery. Desirably, at least one of the permeable materials having barrier properties is a spunbond/meltblown/spunbond material.

The present invention also encompasses a method of making a sterilization wrap system. The method includes the steps of: providing a first panel including a permeable material having barrier properties and having a first surface and a second opposing surface, the first panel being substantially opaque or having a first level of translucence; providing a second panel including a permeable material having barrier properties and having a first surface and a second opposing surface, the second panel having a level of translucence that is higher than the translucence of the first panel; and joining the panels together over at least a portion of the their surfaces.

The second panel may be bonded or provided with a plurality of bond points and the bond points define discrete locations having higher translucence than locations on the permeable material of the second panel that are not bond points. The first panel and the second panel may be provided as a single sheet of permeable material having barrier properties, the single sheet may then be folded over to form a first panel and second panel and at least the edges opposite the fold joined together. Alternatively, the first panel and the second panel may be provided as independent sheets of material which may be joined together. For example, the first panel and second panel may each have a periphery and the first panel and second panel may be overlaid and joined at the periphery.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Invention with reference to the accompanying drawing figures, in which like reference numerals denote similar structure and refer to like elements throughout, and in which.

DEFINITIONS

Figure 1:
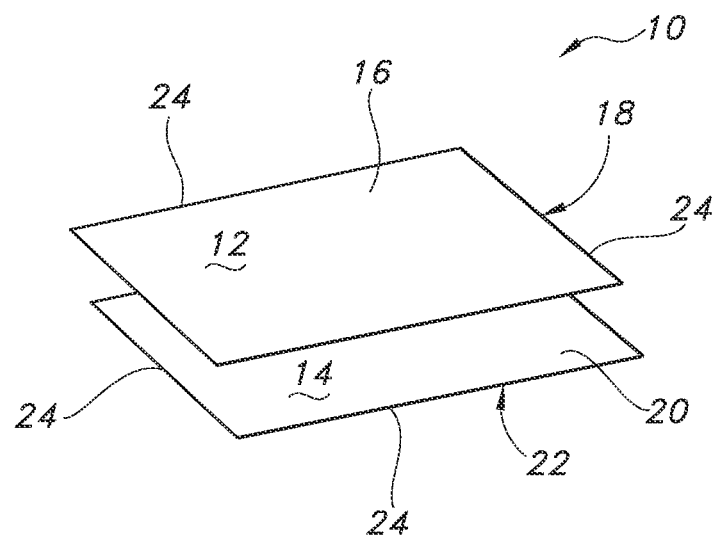
FIG. 1 is a perspective view illustration of an exemplary sterilization wrap system.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "sterilization wrap" refers to a flexible article composed of fabric(s) and/or flexible material (s) that is wrapped around, folded around or otherwise encloses a non-sterile article or non-sterile content prior to sterilization. A sterilization wrap may have multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding and bonded carded web processes.

As used herein, the term "spunbonded web" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbonded nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, "ultrasonic bonding" means a process performed, for example, by passing the fabric between a sonic horn and anvil roll as illustrated in U.S. Pat. No. 4,374,888 to Bornslaeger, the entire contents of which is incorporated herein by reference.

As used herein "point bonding" means bonding one or more layers of fabric at a plurality of discrete bond points. For example, thermal point bonding generally involves passing a fabric or web of fibers to be bonded between a heated roll assembly such as, for example, a heated calender roll and an anvil roll. The calender roll is usually patterned in some way so that the entire fabric is not bonded across its entire surface, and the anvil roll is usually smooth. As a result, various patterns for calender rolls have been developed for functional and/or aesthetic reasons. One example of a pattern has points and is the Hansen Pennings or "H&P" pattern with about a 30% bond area with about 200 bonds/square inch (31 bonds/square cm) as taught in U.S. Pat. No. 3,855,046 to Hansen and Pennings. Another example is shown in U.S. Design Pat. No. 239,566 to Vogt. Typically, the percent bonding area varies from around 5% to around 30% of the area of the fabric laminate web. Spot bonding holds the laminate layers together as well as imparts integrity to each individual layer by bonding filaments and/or fibers within each layer without destroying the breathability or hand of the fabric.

As used herein "opacity" means the optical density of a material and is the opposite of transparency. A material having high opacity or which is opaque has good hiding or covering power in that it can conceal another article, tint or shade over which it is applied. A material having greater opacity will have greater impenetrability to electromagnetic radiation in the visible spectrum. A substantially opaque material will allow very little light to pass through. For example, the light transmittance (visible spectrum) of a substantially opaque material such as a substantially opaque nonwoven fabric will generally be less than about 25% as measured using a conventional color meter spectrophotometer such as, for example, a HunterLab D25 optical sensor and a HunterLab DP-9000 processor available from HunterLab Associates, Inc., Reston, Virginia. As another example, the light transmittance of a substantially opaque nonwoven fabric will generally be less than about 20%. As yet another example, the light transmittance of a substantially opaque nonwoven fabric will generally be less than about 15%. Desirably, the light transmittance of a substantially opaque nonwoven fabric will generally be less than about 10% and may be between 10% and 5%.

As used herein, "translucence" or "translucent" means the light transmittance or optical density of a material which is in a range between substantially transparent and substantially opaque. Generally speaking, translucent materials allow light to pass through diffusely whereas substantially transparent materials appear clear. A material that is translucent will allow a greater level of electromagnetic radiation in the visible spectrum to pass through it than an opaque or substantially opaque material but will allow a lower level of electromagnetic radiation in the visible spectrum to pass through it than a transparent or substantially transparent material. For example, the light transmittance (visible spectrum) of a translucent material such as a nonwoven fabric having translucence and a satisfactory level of barrier properties will generally be greater than about 30% as measured using a conventional color meter spectrophotometer such as, for example, a HunterLab D25 optical sensor and a HunterLab DP-9000 processor available from HunterLab Associates, Inc., Reston, Virginia. The light transmittance is expressed as a percentage and determined using the following formula: Light Transmittance=(100−Percent Opacity). Thus, a material having a percent opacity of 70% has a light transmittance of 30%. As another example, the light transmittance of a nonwoven fabric having translucence and a satisfactory level of barrier properties will generally be greater than about 35%. As yet another example, the light transmittance of a nonwoven fabric having translucence and a satisfactory level of barrier properties will generally be greater than about 40% (e.g., 50%, 60% or even 70%). Desirably, the light transmittance of a nonwoven fabric having translucence and a satisfactory level of barrier properties will generally be from about 30% to about 60%.

DETAILED DESCRIPTION OF INVENTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Figure 2:
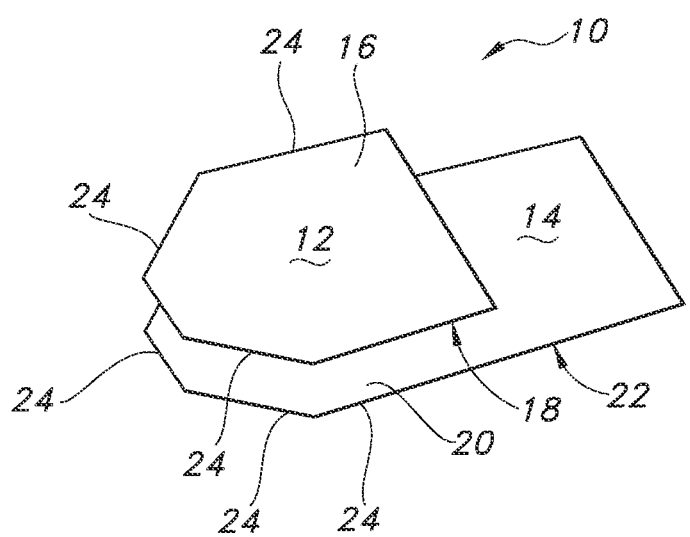
FIG. 2 is a perspective view illustration of another exemplary sterilization wrap system.

Referring now to FIG. 1, there is shown an exemplary sterilization wrap system 10 which includes an exterior panel 12 and an interior panel 14. FIG. 2 is an illustration of another exemplary sterilization wrap system which may be in the form of a multi-panel sterilization assembly such as described in U.S. Patent Application Publication No. US2011/0033137A1 for a "Flexible Multi-Panel Sterilization Assembly" published on Feb. 10, 2011, the entire contents of which are incorporated herein by reference. Referring to FIG. 2, the sterilization wrap system 10 may have an exterior panel 12 and a second panel 12. Other details of the assembly are not shown to simplify the description.

The exterior panel 12 is made of or includes a permeable material having barrier properties and has a first surface 16 and a second opposing surface 18. The exterior panel 12 may be substantially opaque or will have a first level of translucence. The interior panel 14 is made of or includes a permeable material having barrier properties and has a first surface 20 and a second opposing surface 22. The interior panel 14 has a level of translucence that is higher than the translucence of the first panel. The panels may be joined together over at least a portion of their surfaces.

In an aspect of the invention, the permeable material of the interior panel 14 may be a permeable material that has a higher level of translucence than the permeable material of the exterior panel 12. For example, the difference in translucence as expressed in terms of light transmittance between first panel and the second panel may be at least 15 percent. As another example, the difference in translucence between first panel and the second panel may be at least 30 percent. As yet another example, the difference in translucence between first panel and the second panel may be at least 45 percent. The difference in translucence between first panel and the second panel may be 75 percent or more. For example, the difference in translucence between first panel and the second panel may be 250 percent or more. As another example, the difference in translucence between first panel and the second panel may be 500 percent or more.

Referring now to FIGS. 3-6, there is illustrated (not to scale) the interior panel 14 and a plurality of bond points 100 that may be located on the second panel. These bond points 100 define discrete locations having higher translucence than locations 102 on the permeable material of the second panel that are not bond points. This may be best illustrated in FIGS. 3 and 6. The exterior panel 12 may be similarly bonded.

One characteristic of the second panel is that it has a total bond area of about 30 percent and a relatively uniform bond density of greater than about 100 bonds per square inch. For example, the second panel may have a total bond area from about 10 to about 40 percent (as determined by conventional optical microscopic methods) and a bond density from about 100 bonds to about 500 pin bonds per square inch.

Such a combination total bond area and bond density may be achieved by bonding the continuous filament substrate with a pin bond pattern having more than about 100 pin bonds per square inch which provides a total bond surface area less than about 30 percent when fully contacting a smooth anvil roll. Desirably, the bond pattern may have a pin bond density from about 150 to about 250 pin bonds per square inch and a total bond surface area from about 10 percent to about 25 percent when contacting a smooth anvil roll.

One example of a pattern is the Hansen Pennings or "H&P" pattern with about a 30% bond area with about 200 bonds/square inch (31 bonds/square cm) as taught in U.S. Pat. No. 3,855,046 to Hansen and Pennings, the contents of which are incorporated by reference. Another example is shown in U.S. Design Pat. No. 239,566 to Vogt and illustrated in FIG. 3 above which is identified as the "RHT" pattern. The bond area for the RHT pattern is about 20%+ 10%. Typically, the percent bonding area varies from around 5% to around 30% of the area of the fabric laminate web.

Figure 4:
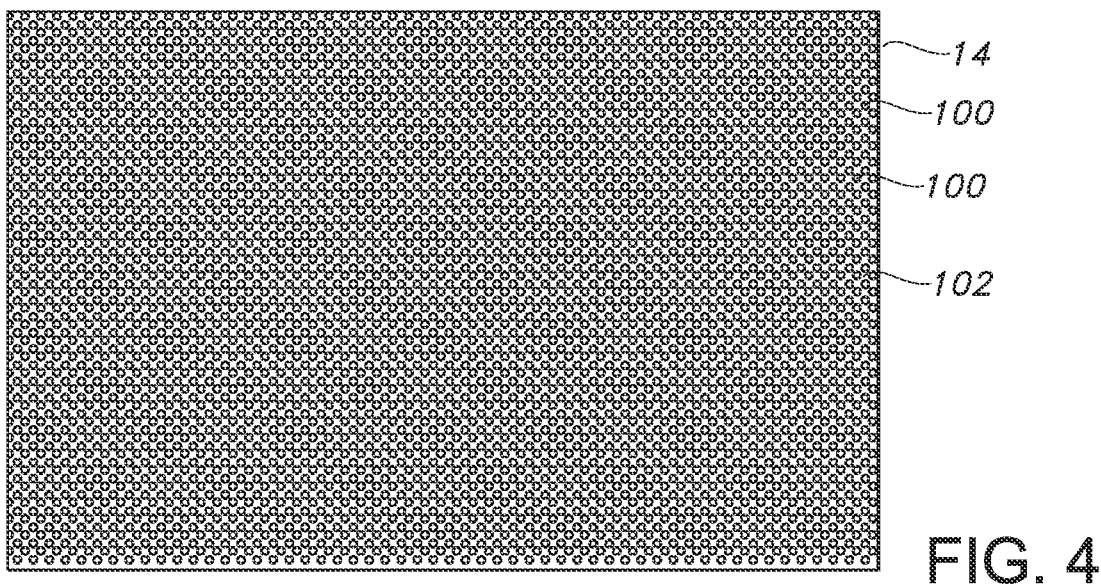
FIG. 4 is top view illustration of another exemplary bond pattern.
Figure 5:
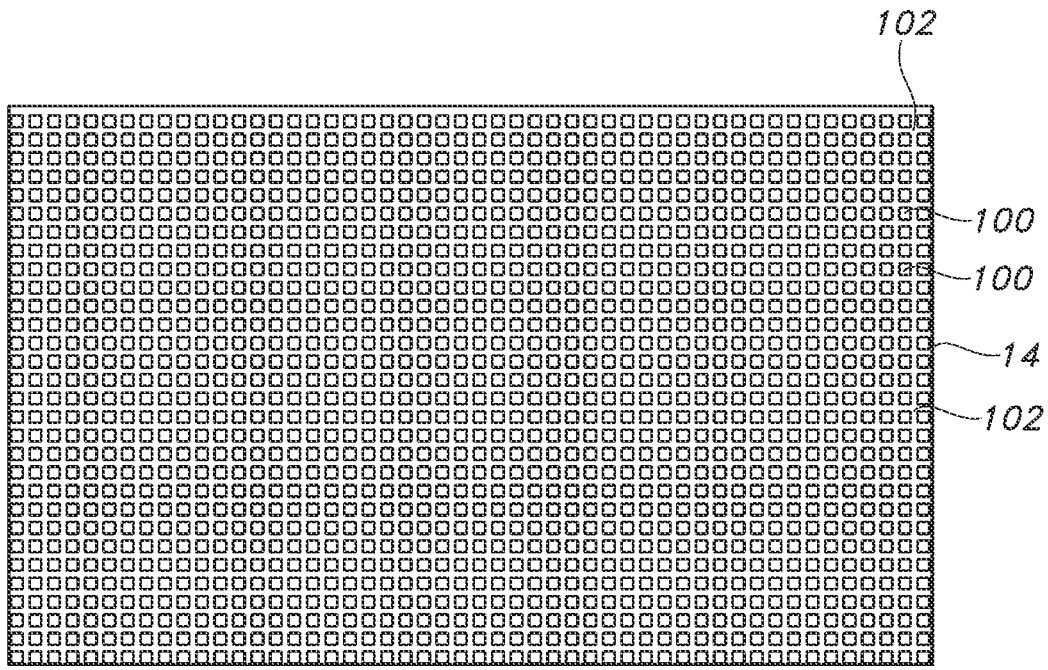
FIG. 5 is top view illustration of another exemplary bond pattern.
Figure 6:
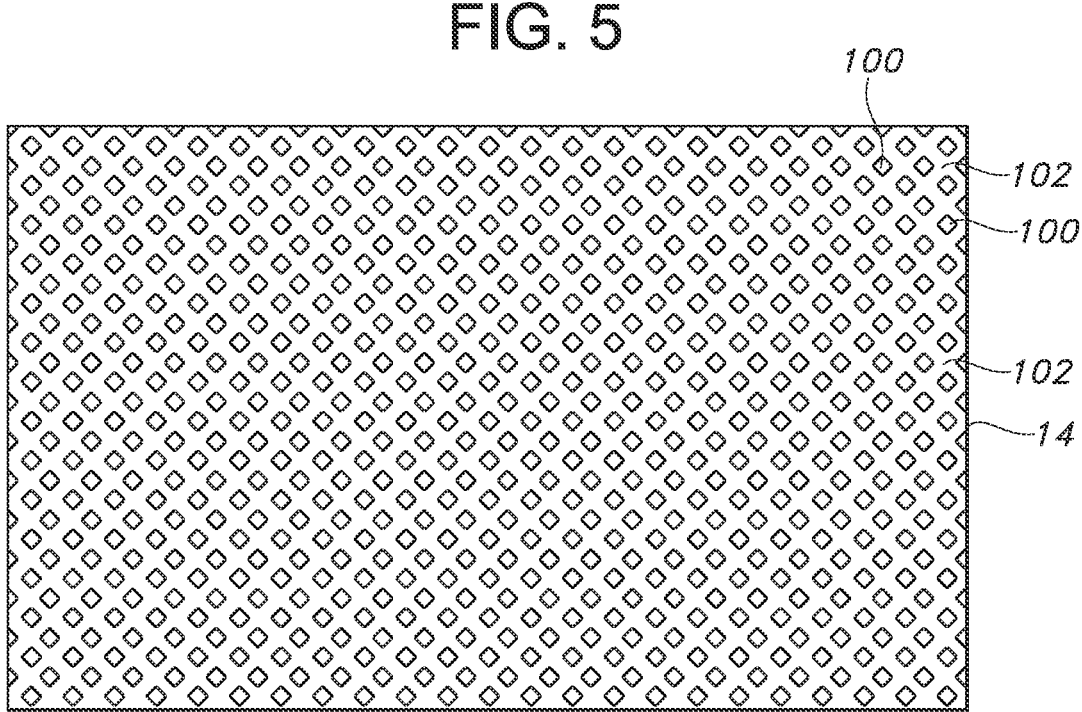
FIG. 6 is top view illustration of another exemplary bond pattern.

An exemplary bond pattern is shown in FIG. 4 (714 pattern). That bond pattern has a pin density of about 306 pins per square inch. Each pin defines square bond surface having sides which are about 0.025 inch in length. When the pins contact a smooth anvil roller they create a total bond surface area of about 15.7 percent. High basis weight substrates generally have a bond area which approaches that value. Lower basis weight substrates generally have a lower bond area. FIG. 5 is another exemplary bond pattern (WW13 pattern). The pattern of FIG. 5 has a pin density of about 278 pins per square inch. Each pin defines a bond surface having 2 parallel sides about 0.035 inch long (and about 0.02 inch apart) and two opposed convex sides—each having a radius of about 0.0075 inch. When the pins contact a smooth anvil roller they create a total bond surface area of about 17.2 percent. FIG. 6 is another bond pattern which may be used. The patter of FIG. 6 has a pin density of about 103 pins per square inch. Each pin defines a square bond surface having sides which are about 0.043 inch in length. When the pins contact a smooth anvil roller they create a total bond surface area of about 16.5 percent.

According to the invention, the plurality of bond points 100 on the interior panel 14 may provide the second panel with at least 15 percent higher translucence than locations 102 on the permeable material of the second panel that are not bond points. As another example, the plurality of bond points on the second panel may provide the second panel with at least 30 percent higher translucence. As yet another example, plurality of bond points on the second panel may provide the second panel with at least 45 percent higher translucence. As yet another example, the difference in translucence may be 75 percent or more. For example, the difference in translucence may be 250 percent or more. As another example, the difference in translucence may be 500 percent or more.

Desirably, the sterilization system is adapted for use in steam sterilizing conditions, ethylene oxide sterilizing conditions, as well as other conventional sterilizing systems.

According to an aspect of the invention, the exterior panel 12 and the interior panel 14 may be a single sheet of permeable material having barrier properties and the single sheet being folded to form an exterior panel 12 and interior panel 14 and at least the edges opposite the fold being joined together. In another aspect of the invention, the exterior panel 12 and the interior panel 14 may be independent sheets of material that are joined together. For example, the exterior panel 12 and interior panel 14 may each have a periphery 24 and the exterior panel 12 and interior panel 14 may be overlaid and joined at the periphery 24. Desirably, at least one of the permeable materials having barrier properties is a spunbond/meltblown/spunbond material.

In important aspect of the present invention is the method of using a sterilization wrap system. The method includes the steps of providing an article and then wrapping the article with a sterilization wrap system 10 having an exterior (or first) panel 12 including a permeable material having barrier properties and having a first surface 16 and a second opposing surface 18, the exterior panel 12 being substantially opaque or having a first level of translucence; and an interior (or second) panel 14 including a permeable material having barrier properties and having a first surface 20 and a second opposing surface 22, the interior panel 14 having a level of translucence that is higher than the translucence of the exterior panel 12, the panels being joined together over at least a portion of their surfaces.

The method further includes the steps of exposing the wrapped article to sterilizing conditions for a sufficient time such that the article is sterilized. The sterilized article may be stored or it may be delivered to an operating room or other location. The method includes the step of unwrapping the article and removing the sterilization wrap system.

Figure 7:
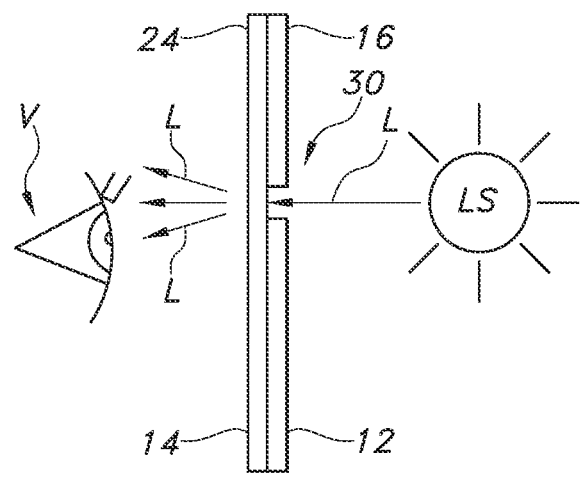
FIG. 7 is a side view illustration of an exemplary method of using or inspecting a sterilization wrap system.

Referring now to FIG. 7, the method includes the step of positioning the sterilization wrap system 10 so at least a portion of the exterior panel 12 of the sterilization wrap system 10 is opposite a viewer "V" and a corresponding portion of the interior panel 14 is facing a viewer "V"; and inspecting the sterilization wrap system 10 for breaches 30 in the exterior panel 12 by looking for light "L" passing through the interior panel 14 facing the viewer.

Figure 8:
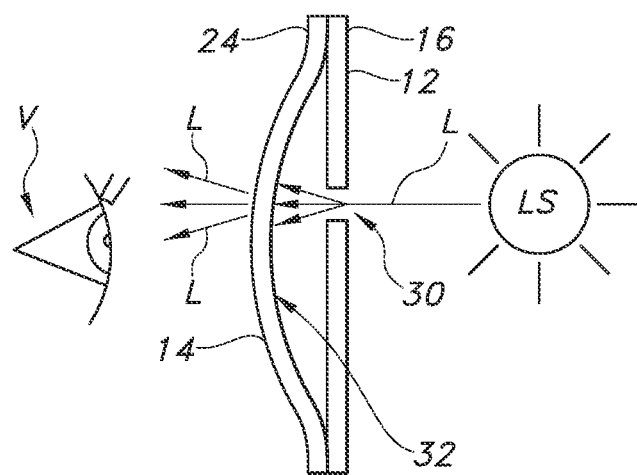
FIG. 8 is a side view illustration of another exemplary method of using or inspecting a sterilization wrap system.

The sterilization wrap system is desirably positioned so that the sterilization wrap system is located between a light source "LS" and a viewer "V". In an aspect of the invention illustrated in FIG. 8, the sterilization wrap system 10 may be positioned or held or manipulated so that the first panel and the second panel are separated by a space 32 in a portion of the sterilization wrap system being inspected.

According to the invention, the second panel may include a plurality of bond points 100 and the bond points define discrete locations having higher translucence than locations 102 on the permeable material of the interior panel 14 (or second panel) that are not bond points such that inspecting the sterilization wrap system for exterior panel breaches is carried out by looking for light passing through the interior panel 14 facing the viewer by way of one or more bond points.

The present invention also encompasses a method of inspecting a sterilization wrap system 10 for breaches after it is removed from an article. The method includes the steps of: positioning a sterilization wrap system 10 with respect to a viewer (that is, a sterilization wrap system including an exterior panel 12 composed of a permeable material having barrier properties and having a first surface 16 and a second opposing surface 18, the exterior panel 12 being substantially opaque or having a first level of translucence; and a interior panel 14 composed of a permeable material having barrier properties and having a first surface 20 and a second opposing surface 24, the interior panel 14 having a level of translucence that is higher than the translucence of the exterior panel 12, wherein the panels are joined together over at least a portion of their surfaces and wherein at least a portion of one panel of the sterilization wrap system 10 is opposite a viewer "V" and a corresponding portion of the other panel is facing a viewer "V"); and inspecting the sterilization wrap system 10 for breaches 30 in a panel by looking for light "L" passing through the panel facing the viewer "V".

The sterilization wrap system is desirably positioned so that the sterilization wrap system 10 is located between a light source "LS" and a viewer "V". In an aspect of the invention, the sterilization wrap system 10 may be positioned so that the exterior panel 12 and the interior panel 14 are separated by a space 32 in a portion of the sterilization wrap system being inspected.

According to another aspect of the invention, the exterior panel 12, the interior panel 14 or both panels (12 and 14) may include a plurality of bond points 100 and the bond points define discrete locations having higher translucence than locations 102 on the permeable material of the respective first or second panel that are not bond points such that inspecting the sterilization wrap system for breaches in a panel is carried out by looking for light "L" passing through the panel facing the viewer "V" by way of one or more bond points 100. According to the invention, the exterior panel 12 may be opposite the viewer "V" and the interior panel 14 may be facing the viewer "V". Alternatively, the exterior panel 12 may be facing the viewer "V" and the interior panel 14 may be opposite the viewer "V".

The present invention also encompasses a method of making a sterilization wrap system. The method includes the steps of: providing an exterior panel 12 including a permeable material having barrier properties and having a first surface 15 and a second opposing surface 18, the exterior panel 12 being substantially opaque or having a first level of translucence; providing an interior panel 14 including a permeable material having barrier properties and having a first surface 20 and a second opposing surface 22, the interior panel 14 having a level of translucence that is higher than the translucence of the exterior panel 12; and joining the panels together over at least a portion of the their surfaces.

The second panel may be bonded or provided with a plurality of bond points 100 and the bond points define discrete locations having higher translucence than locations 102 on the permeable material of the second panel that are not bond points. The exterior panel 12 and the interior panel 14 may be provided as a single sheet of permeable material having barrier properties. The single sheet may then be folded over to form an exterior panel 12 and interior panel 14 and at least the edges opposite the fold joined together. Alternatively, the first panel and the second panel may be provided as independent sheets of material which may be joined together. For example, the exterior panel 12 and interior panel 14 may each have a periphery 25 and the first panel and second panel may be overlaid and joined at the periphery 24.

Examples

Aspects of the invention were evaluated in the following examples.

An exemplary wrap was made from two stacked panels (also refers to as "plies" or individually as "ply") of gas permeable nonwoven fabric. Each ply/panel of the fabric had barrier properties with respect to microbe contaminates. Each ply also was made from polypropylene or other dimensionally stable thermoplastic polymers at temperature typical of steam sterilization (they do not shrink). In addition, each ply/panel had relative differences in color: one lighter than the other. The opacity of the interior ply (which was lighter colored) was less than the exterior ply. In this example, each play was thermally bonded so that the bonded areas become more translucent (less opaque) than the unbonded areas.

Exemplary plies or panels are laminate material composed of thermally point bonded layers of spunbond material sandwiching a layer of meltblown material (also referred to as "SMS" material). One ply forms the exterior side, (to be the outside of the wrap when enveloping contents) and the other ply forms the interior side (to be the inside of the wrap when enveloping contents); The exterior ply is a dark color (e.g. blue) relative to the interior ply (e.g. white) so that the interior ply always has less opacity than the exterior ply.

This stacking arrangement of a dark colored exterior ply against a lighter colored interior ply makes a breach in the exterior ply, e.g. due to a tear or hole in the exterior ply, easier to detect through the interior ply compared to two stacked plies of the same color.

The invention is illustrated via an exterior ply of SMS that is blue against an interior ply of similar dimensioned SMS that is white and less opaque (i.e., more translucent), and the plies are attached together at least near one common edge. Examples of suitable exterior and interior SMS plies are shown in Table 1. The basis weight is reported in ounces per square yard (osy)—which may be converted to grams per square meter by multiplying the osy value by 33.91. The amount of meltblown (MB) in the SMS ranges from 14 to 35%.

TABLE 1

| Example | Ply Target Color | Basis Weight (osy) | SB layer 1 (osy) | MB center layer (osy) | SB layer 2 (osy) | % MB |
| --- | --- | --- | --- | --- | --- | --- |
| Exterior1 | Light Blue | 1.05 | 0.378 | 0.294 | 0.378 | 28% |
| Exterior2 | Light Blue | 1.20 | 0.432 | 0.336 | 0.432 | 28% |
| Exterior3 | Mid-range Blue | 1.40 | 0.455-0.504 | 0.392-0.490 | 0.455-0.504 | 28-35% |
| Exterior4 | Mid-range Blue | 1.85 | 0.694-0.759 | 0.333-0.463 | 0.694-0.759 | 18-25% |
| Exterior5 | Dark Blue | 2.05 | 0.769-0.851 | 0.349-0.513 | 0.769-0.851 | 17-25% |
| Exterior6 | Dark Blue | 2.57 | 0.964-1.106 | 0.360-0.643 | 0.964-1.106 | 14-25% |
| Interior1 | White | 1.05 | 0.378 | 0.294 | 0.378 | 28% |
| Interior2 | White | 1.20 | 0.432 | 0.336 | 0.432 | 28% |
| Interior3 | White | 1.40 | 0.455-0.504 | 0.392-0.490 | 0.455-0.504 | 28% |
| Interior4 | White | 1.85 | 0.694-0.759 | 0.333-0.463 | 0.694-0.759 | 18-25% |
| Interior5 | White | 2.05 | 0.769-0.851 | 0.349-0.513 | 0.769-0.851 | 17-25% |
| Interior6 | White | 2.57 | 0.964-1.106 | 0.360-0.643 | 0.964-1.106 | 14-25% |

The relative opacity (Opacity), or conversely translucence (which is expressed as Translucence=100−percent opacity), of Exterior and Interior Example plies from Table 1 and selected stacked combinations were measured via a conventional color meter spectrophotometer. One suitable spectrophotometer is a HunterLab D25 optical sensor and a HunterLab DP-9000 processor available from HunterLab Associates, Inc., Reston, Va. The D25 optical sensor detects red, green, and blue signal data and the DP-9000 processor receives the signal data and converts the data into X, Y, and Z values per the CIE Tristimulus XYZ Scale. Equipment set-up followed conventional practices except that the specimen port was reduced to 0.75 inch diameter opening via an area view insert (also available from HunterLab Associates, Inc.). Appropriate black glass and white calibrated tiles were used for standardization procedures and for taking measurements per the manufacturer's instructions or other accepted standards of practice. Measurements were taken using 2 colorimeter units, 1 & 2, in different locations but otherwise of the same make and model.

The above spectrophotometer arrangement yields a Y value for a sample placed over the reduced specimen port backed by the black glass and another Y value for the same placed sample backed by the white tile; comparing these Y values according "contrast ratio method" yields "opacity" for the sample. The contrast ratio method divides the Y value for the sample backed by the black glass by the Y value for the same sample backed by the white tile, and this ratio is then multiplied by 100.

Figure 9:
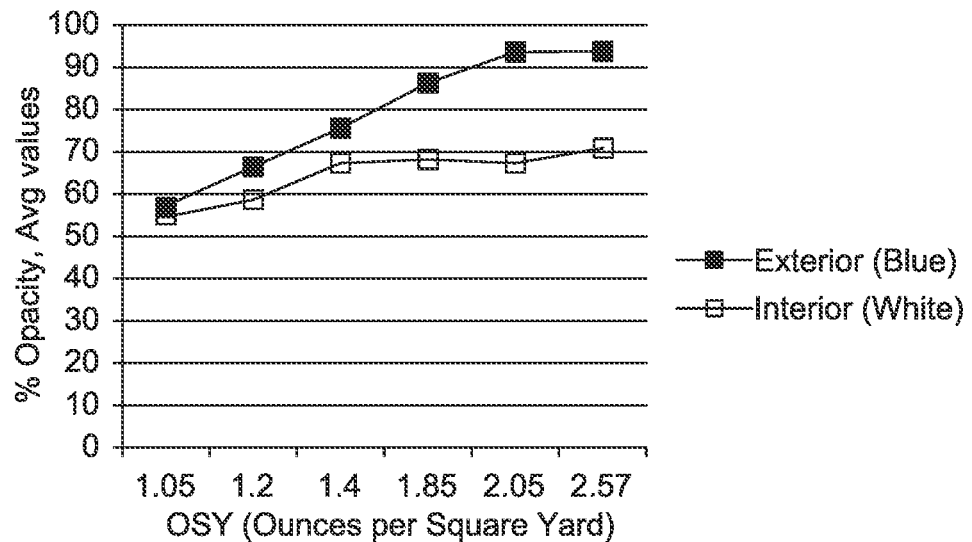
FIG. 9 is an illustration of a graph of data and information from Table 2.

Table 2 lists the Opacity values averaged for the samples of the Table 1 Examples (each as a single ply) and FIG. 9 is a graph illustrating their relationship via the Avg values; at equivalent basis weights the Interior Examples (white) have less opacity than the Exterior Examples (blue). The averages for Colorimeter 1 are of two samples, those for Colorimeter 2 are three samples, and the Avg values represent the average of all five samples.

TABLE 2

Relative Opacity

| Basis Wgt, osy | Exterior Examples (SMS Blue) Colorimeter | | | Interior Examples (SMS White) | | |
|---|---|---|---|---|---|---|
| | 1 | 2 | Avg | 1 | 2 | Avg |
| 1.05 | 56.845 | — | 56.845 | 54.915 | — | 54.915 |
| 1.2 | 66.355 | 66.433 | 66.402 | 58.94 | 58.567 | 58.716 |
| 1.4 | 78.080 | 74.083 | 75.682 | 68.085 | 66.707 | 67.258 |
| 1.85 | 87.900 | 85.223 | 86.294 | 69.975 | 67.027 | 68.206 |
| 2.05 | 94.255 | 93.187 | 93.614 | 67.725 | 67.207 | 67.414 |
| 2.57 | 94.150 | 93.463 | 93.738 | 71.765 | 70.537 | 71.028 |

Samples representative of the invention were made by stacking an Interior ply (white) on top of an Exterior ply (blue). Comparative samples were also made by stacking 2 plies on the same color one on top of the other and reversing the arrangement of the samples of the invention (blue on top of white).

In order to demonstrate the aspect of the present invention related to facilitating breach detection in the Exterior ply by detection of light through the Interior ply, a 1.4 mm hole diameter was made (via a pointed rod) in selected Exterior plies for the samples representative of the invention. A 1.4 mm hole diameter was made (via a pointed rod) in selected Exterior plies for the comparative examples as well.

Figure 10:
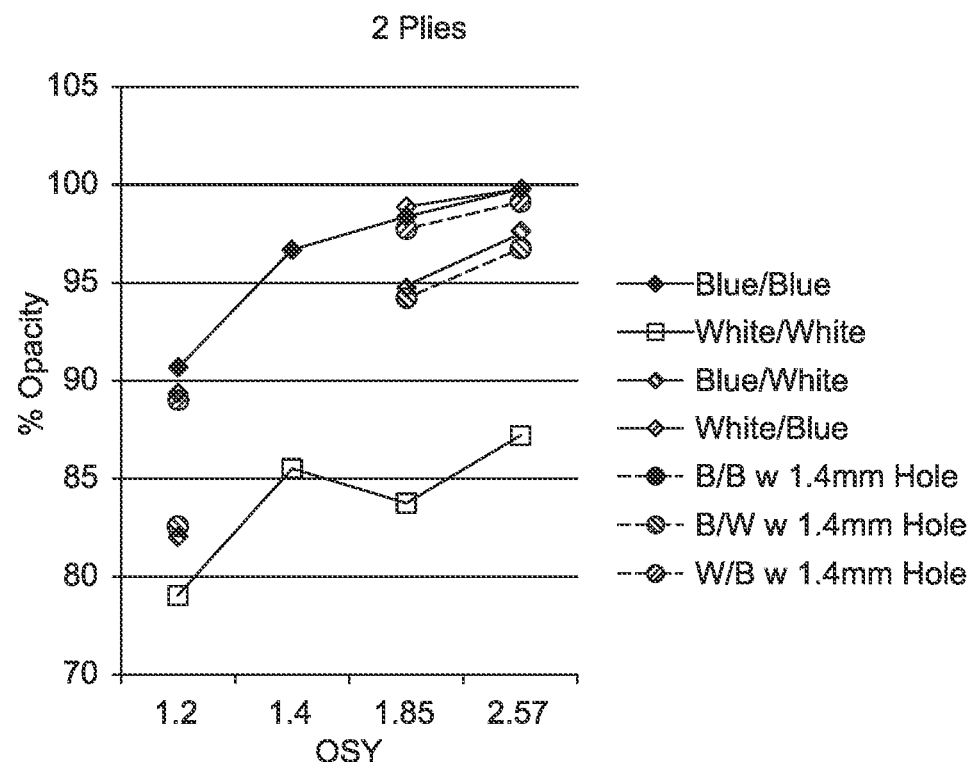
FIG. 10 is an illustration of a graph of data and information from Table 3.

Opacity measurements were made for the stacked 2 plies with the Exterior ply immediately placed against the specimen port of the spectrometer, the Interior ply above the Exterior ply, and the backing plate (black glass, the white tile) on top. The samples and their Opacity values are listed in Table 3; values for Colorimeter 1 represent individual measurements; values for Colorimeter 2 represent an average of at least two measurements. Their relationships are shown using the averaged Colorimeter 2 averages when possible in FIG. 10 of the drawings.

TABLE 3

| | | Opacity for 2 plies, each ply at: | | | | |
|---|---|---|---|---|---|---|
| | | 1.2 osy | | 1.85 osy | 2.56 osy | |
| Description of | | Colorimeter | | | | |
| Exterior/Interior | | 1 | 2 | 1 | 1 | 2 |
| Invention Set | Blue/White | 82.55 | 82.02 | 94.71 | 98.51 | 97.62 |
| Comp. Set 1 | White/Blue | 90.31 | 89.35 | 98.9 | 97.84 | 99.74 |
| Comp. Set 2 | Blue/Blue | 90.68 | — | 98.39 | 99.79 | — |
| Comp. Set 3 | White/White | 79.04 | — | 83.8 | 87.21 | — |
| Invention Set with breach | B/W w 1.4 mm Hole | 82.92 | 82.55 | 94.22 | 96.88 | 96.78 |
| Comp Set 1 with breach | W/B w 1.4 mm Hole | 90.17 | 89.03 | 97.71 | 99.78 | 99.11 |
| Comp. Set 2 with breach | B/B w 1.4 mm Hole | — | — | 97.85 | 99.55 | — |

The information in Tables 4-6 highlight the improvement in translucence provided by point bonding. The point bonding for all the samples used the same bonding pattern, the RHT pattern, which imparted ~20% bonded area (80% remaining unbonded).

Table 4A lists the Opacity values per: Colorimeter 1 as averages of two samples, except as noted by an asterisk (*); Colorimeter 2 as averages of three samples; and Avg as the average of Colorimeter 1 & 2 measurements. The different types of samples tested were: 100% white polypropylene meltblown fabric (MB) at different basis weights that were unbonded (i.e., no bonded regions); a 100% white polypropylene MB having a basis weight of 1 osy that was thermally point bonded; and a sample of the Blue Exterior Example at 2.57 osy (a retest to determine reproducibility of Table 2 Opacity values). The asterisk (*) represents Opacity values for only one sample per Colorimeter 1.

TABLE 4A

| Sample Number | Description | | | | % Opacity per Colorimeter: | | |
|---|---|---|---|---|---|---|---|
| | Color | Bonded | Fabric | Basis Wgt, osy | 1 | 2 | Avg |
| 7 | White | None | MB | 0.29 | — | 50.59 | 50.59 |
| 8 | White | None | MB | 0.44 | — | 57.82 | 57.82 |
| 9 | White | None | MB | 0.59 | — | 68.45 | 68.45 |
| 10 | White | None | MB | 0.74 | 77.96 | 76.47 | 77.07 |
| 6 | White | None | MB | 1.04 | — | 86.21 | 86.21 |
| 11 | White | None | MB | 1.18 | 87.17 | 84.37 | 85.49 |
| 12 | White | None | MB | 1.62 | 90.61 | 89.69 | 90.06 |
| 5 | White | None | MB | 2.56 | — | 95.25 | 95.25 |
| 13 | White | Point | MB | 1 | 70.57 | 68.78 | 69.50 |
| 14 | Blue | Point | SMS* | 2.57 | 94.09 | 93.46 | 93.62 |

Figure 3:
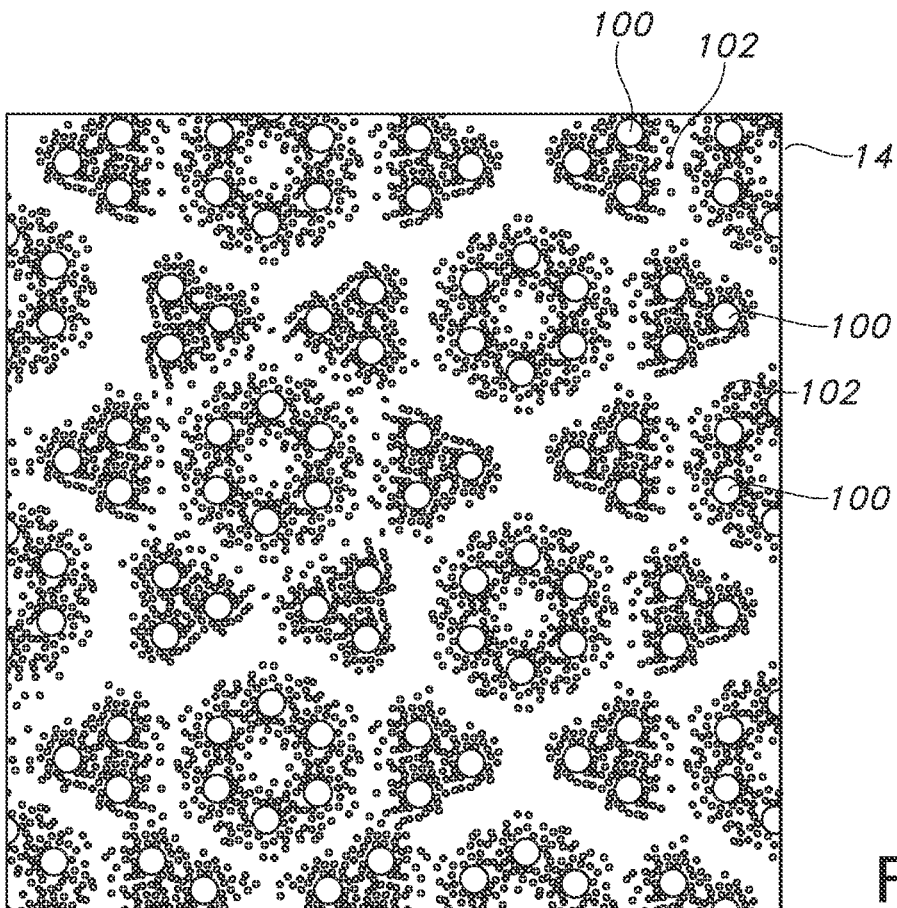
FIG. 3 is top view illustration of an exemplary bond pattern.

Table 4B lists Opacity averages per Colorimeter 2 of three samples for the MB fabric of Sample Number 5-9 after each fabric was thermally point bonded using the pattern of FIG. 3, which matched the pattern for the other Point Bonded fabrics. The Sample Numbers of Table 4B correspond respectively to those of Table 4A (e.g. 7B samples were made from the fabric for Sample Number 7 of Table 4A).

TABLE 4B

| Sample Number | Description | | | Basis Wgt, osy | % Opacity per Colorimeter 2 |
|---|---|---|---|---|---|
| | Color | Bonded | Fabric | | |
| 7B | White | Point | MB | 0.29 | 45.07 |
| 8B | White | Point | MB | 0.44 | 56.58 |
| 9B | White | Point | MB | 0.59 | 63.10 |
| 6B | White | Point | MB | 1.04 | 73.70 |
| 5B | White | Point | MB | 2.56 | 80.72 |

Table 5 lists Opacity values per Colorimeter 1 for samples listed in Table 2 and Table 5 that were subsequently "filmed" so that each sample was 100% bonded. The term "filmed" means that the samples were sandwiched between thin metal foil strips (one rigid for support, the other aluminum foil) and passed through commercially available desktop laminator that heated and pressed the sandwiched sample. The combination of heat and pressure resulted in a fusing of individual fibers and filaments into a sheet that has the appearance of a film. The purpose of this procedure is to determine a level of opacity of the polymeric material that forms the nonwoven fabric (e.g., MB or SMS) by eliminating the fibrous structure formed of individual fibers or filaments in the nonwoven fabric. The asterisk (*) represents Opacity values for only one sample. Samples that are described as "Point and Filmed", the sample initially had Point Bonds present in the material prior to being "filmed". Samples that that are described only as "Filmed" were unbonded materials (i.e., contained no point bonds) prior to being "filmed."

TABLE 5

| Sample Number | Description | | | | Basis Wgt, osy | % Opacity |
|---|---|---|---|---|---|---|
| | Source | Color | Bonded | Fabric | | |
| 15 | Sample 13 | White | Point & Filmed | MB | 1 | 3.875 |
| 16* | Sample 13 | White | Point & Filmed | MB | 1 | 5.19 |
| 17 | Sample 11 | White | Filmed | MB | 1.18 | 2.51 |
| 18 | Sample 12 | White | Filmed | MB | 1.62 | 1.645 |
| 19* | Sample 10 | White | Filmed | MB* | 0.74 | 2.98 |
| 20 | Table 2 Interior Example | White | Point & Filmed | SMS | 1.2 | 27.77 |
| 21 | Table 2 Exterior Example | Blue | Point & Filmed | SMS | 1.2 | 21.465 |
| 22 | Table 2 Interior Example | White | Point & Filmed | SMS | 1.85 | 25.185 |
| 23 | Table 2 Interior Example | White | Point & Filmed | SMS | 1.85 | 30.24 |
| 24 | Table 2 Exterior Example | Blue | Point & Filmed | SMS | 1.85 | 38.135 |
| 25 | Table 2 Interior Example | White | Point & Filmed | SMS | 2.57 | 36.88 |
| 26 | Table 2 Exterior Example | Blue | Point & Filmed | SMS | 2.57 | 64.78 |

Figure 11:
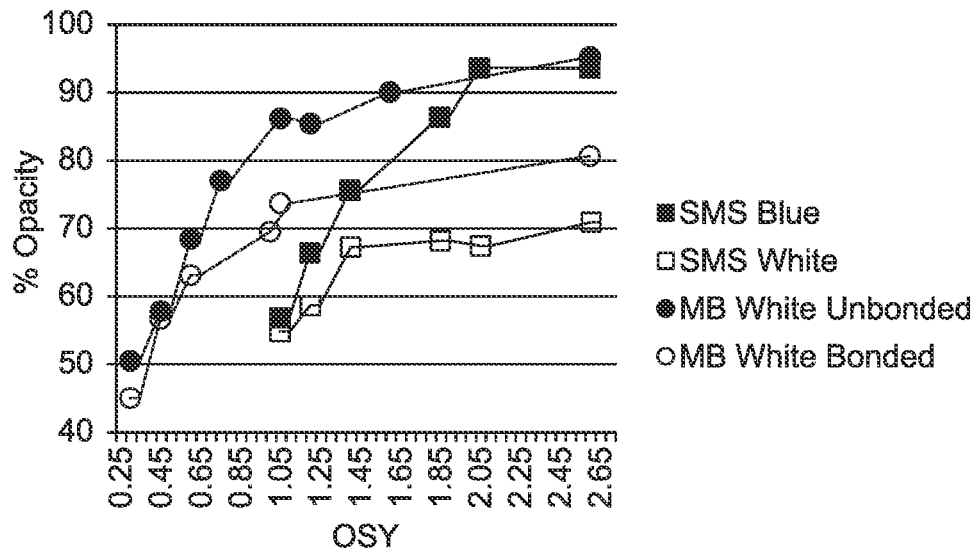
FIG. 11 is an illustration of a graph of data and information from Table 2 and Table 4.

FIG. 11 of the drawings is a graph that compares the Opacity Avg values from Table 2 and Table 4A & B. Examination of these results shows several unexpected results. These are generally as follows:

The unbonded MB samples (identified as MB White Unbonded in FIG. 11) have opacity values higher than the Interior White SMS Examples (identified as SMS White in FIG. 11), even when the basis weight of the unbonded MB is less.

Point bonding of MB decreases the opacity; interpolating an opacity value for an unbonded white MB sample at equivalent weight (i.e. % opacity of 85 from FIG. 11 for MB White at a basis weight of about 1 osy) shows an ~15% difference from the bonded white MB sample (Bonded MB White in FIG. 11).

The opacity contribution by the MB material to the white SMS is a significant factor in opacity.

Figure 12:
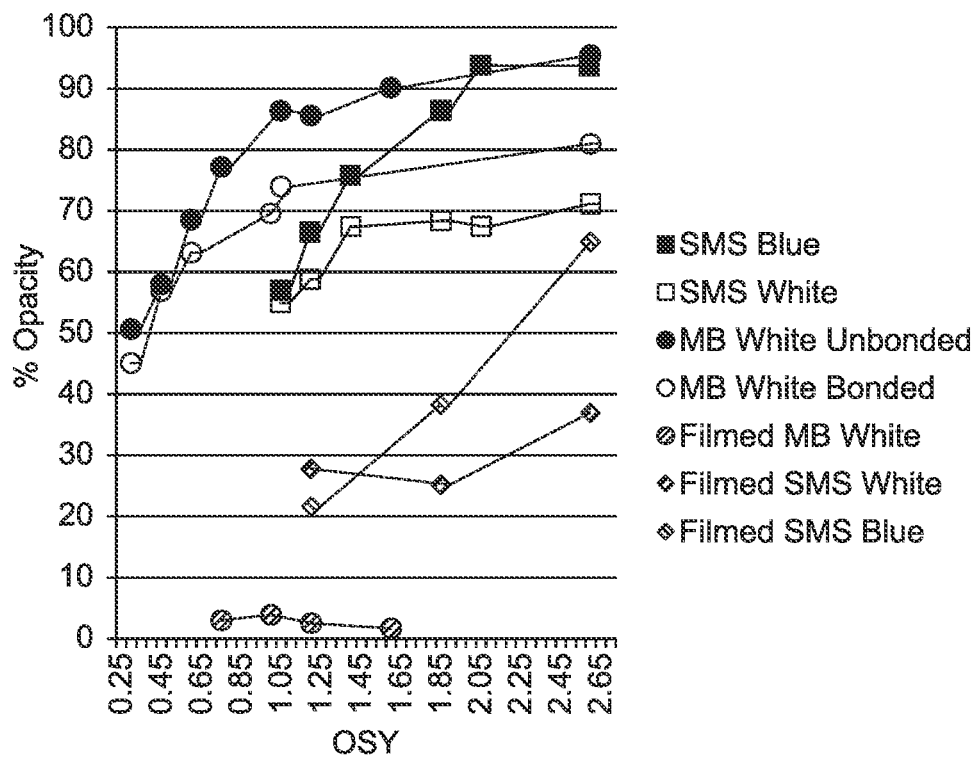
FIG. 12 is an illustration of a graph of data and information from Table 2, Table 4 and Table 5.

FIG. 12 of the drawings is a graph that adds the filmed Opacity values of Table 5 to the Opacity values taken from Tables 2 and 4A&B. Of particular note is that the Opacity for the 100% bonded White MB is essentially unchanged with respect to basis weight. Since the white MB has no pigment added, the filmed MB is clear film. (The opaqueness of the unbounded MB comes from light reflectance off the surfaces of the meltblown fibers.) The filmed SMS white and SMS blue samples indicate the opacity contributions from pigments.

Table 6 lists samples of two stacked plies to illustrate the contribution to the resulting by the MB material. Sample Set 28 of Table 6 represents the Invention Set of Table 3. Sample Set 27 in Table 6 is the "Comp. Set 2" from Table 3. As given in Table 1, the MB contribution is 14-35%. Sample Sets 29, 30, and 31 have significantly more MB contributing to the arrangements of two stacked plies because the weight of each of these 100% MB interior plies is greater than the MB in the interior plies of Sample Set 27 and 28. Their Opacity values per Colorimeter 1 are greater for a given Blue SMS exterior as shown in FIG. 13 of the drawings which is a graph of information from Table 6.

TABLE 6

| Sample | | % OPACITY of 2 stacked plies with SMS components at: | | | |
|---|---|---|---|---|---|
| Set | Description | 1.2 osy | 1.4 osy | 1.85 osy | 2.6 osy |
| 27 | Blue SMS/Blue SMS | 90.68 | 96.655 | 98.39 | 99.785 |
| 28 | Blue SMS/White SMS | 82.55 | — | 94.71 | 98.51 |
| 29 | Blue SMS/Bonded 1 osy White MB | 86.72 | — | 95.02 | 98.03 |
| 30 | Blue SMS/Unbonded 0.74 osy White MB | 89.43 | — | 96.77 | 98.3 |
| 31 | Blue SMS/Unbonded 1.18 osy White MB | 93.86 | — | 96.31 | 100.82 |

Figure 13:
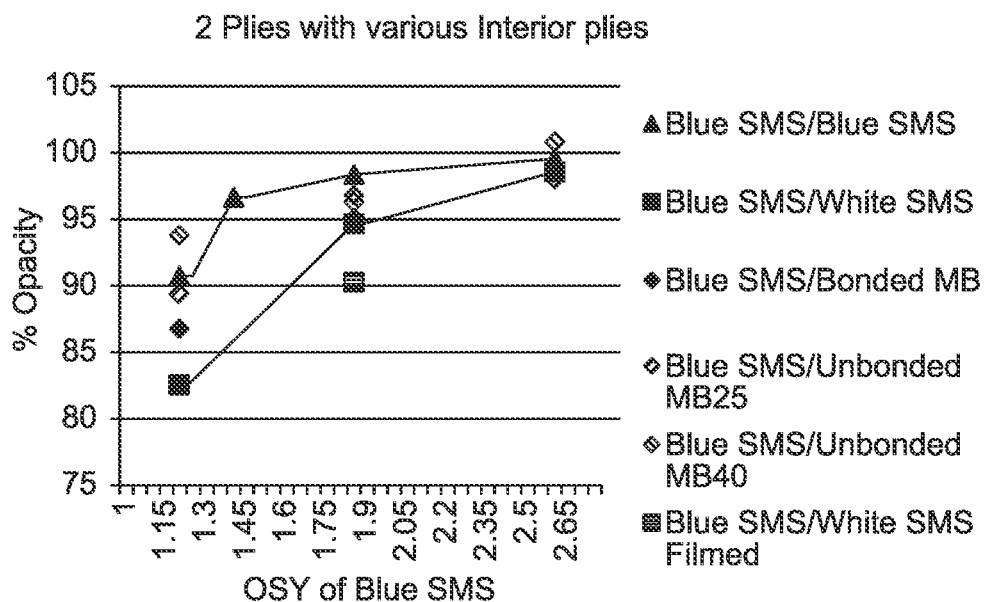
FIG. 13 is an illustration of a graph of data and information from Table 6.

One data point shown in FIG. 13 is for a filmed White SMS as an interior ply stacked on an Exterior Blue SMS ply of 1.85 osy. The filming (creating 100% bonded area as previously described by use of a desktop laminator) shows a decrease in the two stacked plies by an Opacity value of ~5% per Colorimeter 1.

Figure 14:
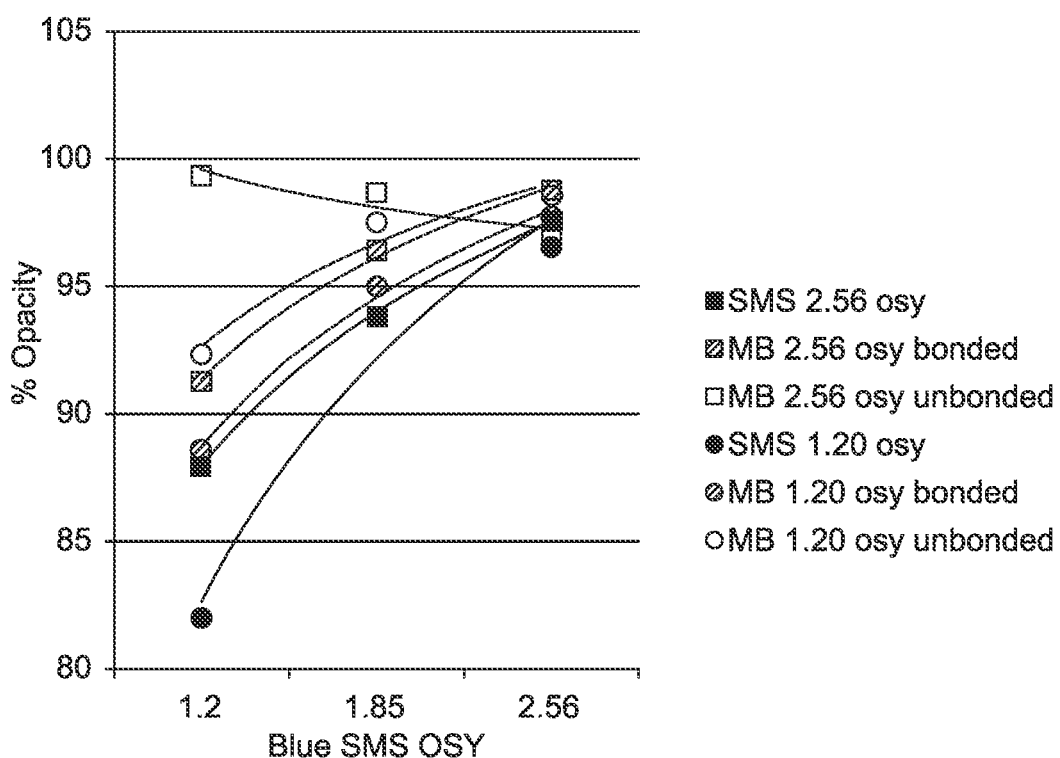
FIG. 14 is an illustration of a graph of data and information from Table 7.

Table 7 lists samples of two stacked plies to further show the impact of MB contribution on the resulting opacity. The Sample Sets listed in this table are made by respectively stacking White interior plies of a given material over Blue exterior SMS plies at three different weights. The opacity values resulted from Colorimeter 2 measurements and are the average of two individual values. Sample Sets 32 and 35 use White SMS as the interior ply; Sample Sets 34 and 37 use White unbonded MB; Sample Sets 33 and 36 use White bonded MB made from the corresponding unbonded MB of Sets 34 and 37 via thermal point bonding with a pattern (of FIG. 3) to match that of the SMS plies. The resulting opacity values listed in the table are depicted in FIG. 14. Both the table and FIG. 14 show that as the MB contribution increases for a given weight, the opacity increases. Also, Table 7 and FIG. 14 show the impact of thermal point bonding the MB: point bonding the MB in the interior ply, which reduces the opacity in that ply (as demonstrated by comparing Table 4A and 4B matching opacity values), corresponding reduces the resulting opacity for the two stacked plies. Thus, white fabrics with thermally point bonded MB components are preferred for plying next to plies of greater opacity for the invention. Especially suited for the invention are white plies that have thermally point bonded MB weight contributions of less than 40%.

TABLE 7

| Sample | | Opacity for White Ply over Blue SMS at OSY: | | |
|---|---|---|---|---|
| Set | White Ply Description | 1.20 | 1.85 | 2.56 |
| 32 | SMS 2.56 osy | 88.00 | 93.84 | 97.62 |
| 33 | MB 2.56 osy bonded | 91.26 | 96.41 | 98.77 |
| 34 | MB 2.56 osy unbonded | 99.35 | 98.705 | 96.91 |
| 35 | SMS 1.20 osy | 82.02 | 93.89 | 96.57 |
| 36 | MB 1.20 osy bonded | 88.56 | 95.00 | 97.74 |
| 37 | MB 1.20 osy unbonded | 92.34 | 97.51 | 98.59 |

Figure 15:
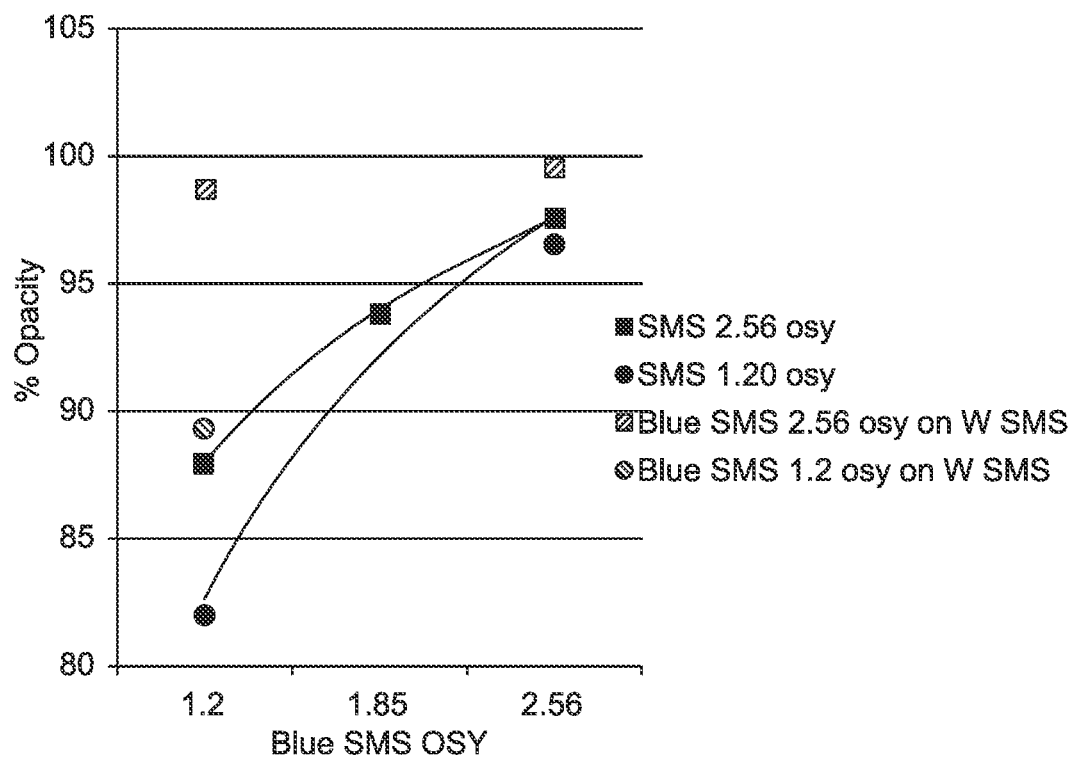
FIG. 15 is an illustration of a graph of data and information from Tables 7 and 8.

The preceding opacity values for the stacked plies result from the Blue SMS immediately over the specimen port and the White ply stacked over the Blue SMS. Reversing the order of these stacked plies changes the resulting opacity. To illustrate this impact (reversing the order on plies on resulting opacity) Table 8 lists opacity values for selected stacking of white and blue SMS plies in the opposite configuration from Table 7: Sample Set 38 reverses the stacking for certain ply arrangements of Sample Set 32; Sample Set 39 reverses the stacking for the 1.20 SMS plies of Sample Set 35. The resulting opacities are the average of two measurements via Colorimeter 2. FIG. 15 graphically compares the opacities of Table 8 to the corresponding related opacities of Table 7; reversing the stacking arrangement results in different opacity values.

TABLE 8

| Sample | Blue Ply | Opacity for Blue Ply over White SMS at OSY: | |
|---|---|---|---|
| Set | Description | 1.20 | 2.56 |
| 38 | SMS 2.56 osy | 98.76 | 99.74 |
| 39 | SMS 1.20 osy | 89.35 | NA |

The impact of the MB contribution on opacity is further detected when a breach in the Blue SMS exists. Tables 9 and 10 give opacity values that are averages of two measurements per Colorimeter 2. For the sample sets, a breach of a 1.4 mm hole was punched (using a rod as previously mentioned) into the Blue SMS plies. The SMS plies for Table 9 are: Blue SMS1 has a weight of 1.20 osy; Blue SMS2 has a weight of 2.56 osy. For Table 9 the White plies respectively stacked next to the Blue SMS plies were all of 2.56 osy but varied in MB contribution or thermal point bonding: Sample Set 40 used unbonded white MB; Sample Set 41 used MB thermally point bonded with the pattern to match that used for the SMS plies; Sample Set 42 used white SMS. For Table 10 the SMS plies include those for Table 9 plus Blue SMS3 that has a weight of 1.85 osy. The White plies of Table 10 were approximately 1.20 osy but varied in MB contribution or thermal point bonding like the White plies of Table 9: Sample Set 43 used unbonded white MB of ~1.10 osy; Sample Set 44 used MB of ~1.10 osy that was thermally point bonded with the pattern to match that used for the SMS plies; Sample Set 45 used white SMS of 1.20 osy. The resulting opacities in Table 9 and 10 were least for the respective white SMS plies (regardless of stacking orientation against the specimen port of the colorimeter).

TABLE 9

| | | Opacity for: | | | |
|---|---|---|---|---|---|
| Sample Set | White Ply Description | Blue SMS1 under White Ply | White Ply under Blue SMS1 | Blue SMS2 under White Ply | White Ply under Blue SMS2 |
| 40 | MB Unbonded 2.56 osy | 97.06 | 99.00 | 98.80 | 99.93 |
| 41 | MB Bonded 2.56 osy | 91.94 | 97.31 | 95.25 | 99.31 |
| 42 | SMS 2.56 osy | 88.36 | 93.57 | 93.29 | 98.33 |

TABLE 10

| | | Opacity for: | | | | | |
|---|---|---|---|---|---|---|---|
| Sample Set | White Ply Description | Blue SMS1 under White | White under Blue SMS1 | Blue SMS3 under White | White under Blue SMS3 | Blue SMS2 under White | White under Blue SMS2 |
| 43 | MB Unbonded ~1.10 osy | 94.11 | 97.22 | 96.53 | 99.55 | 97.98 | 99.43 |
| 44 | MB Bonded ~1.10 osy | 87.36 | 93.20 | 94.39 | 99.06 | 98.47 | 99.14 |
| 45 | SMS 1.20 osy | 82.55 | 89.03 | 91.26 | 97.52 | 96.61 | 99.45 |

Figure 16:
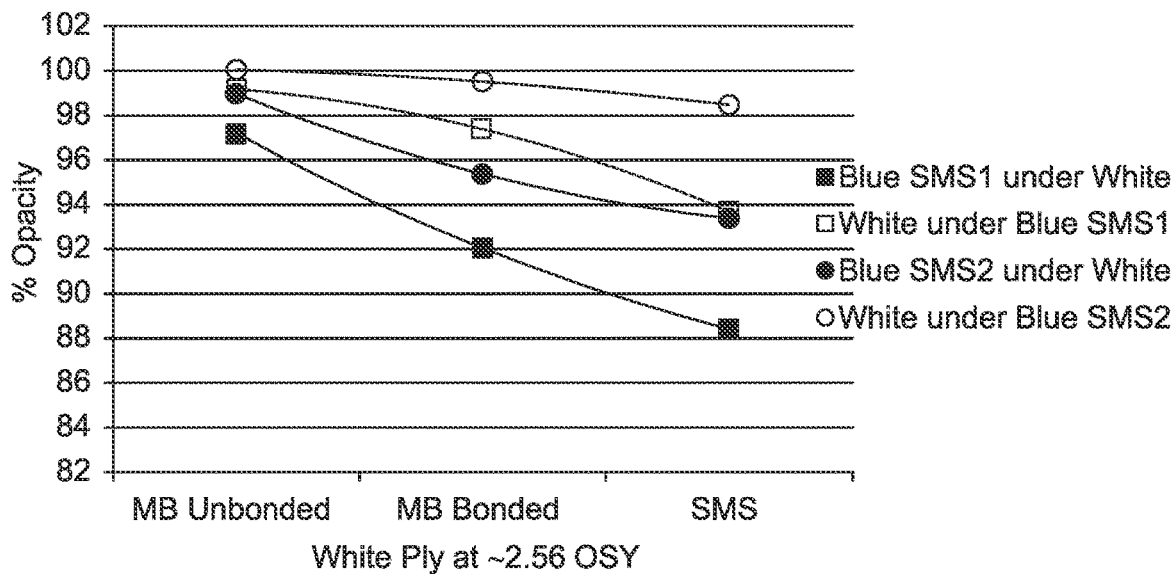
FIG. 16 is an illustration of a graph of data and information from Table 9.
Figure 17:
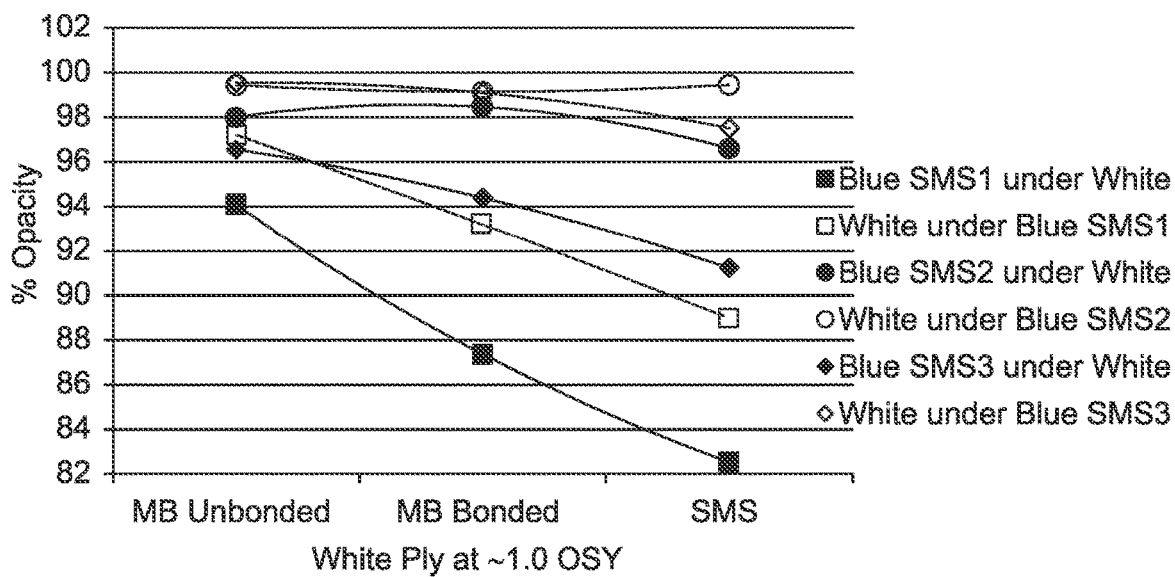
FIG. 17 is an illustration of a graph of data and information from Table 10.

FIGS. 16 and 17 graphically show the respectively show the opacity values of Table 9 and 10 with respect to the type of White ply stacked next to the Blue ply. As shown in FIGS. 16 and 17, the white SMS plies, which have MB % less than 40% and thermal bond points, retain the lowest resulting opacity values when paired next to Blue SMS even with the presence of a breach in the Blue SMS.

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description. The figures are not drawn to scale and related elements may be omitted so as to emphasize the novel features of the invention. Structural and functional details depicted in the figures are provided for the purpose of teaching the practice of the invention to those skilled in the art and are not intended to be considered limitations. Directional terms such as left, right, front or rear are provided to assist in the understanding of the invention and are not intended to be considered as limitations.

While particular embodiments of the present invention have been described herein; it will be apparent to those skilled in the art that alterations and modifications may be made to the described embodiments without departing from the scope of the appended claims.

What is claimed is:

1. A sterilization wrap system comprising:
an exterior panel comprising a permeable nonwoven material having barrier properties and having a first surface and a second opposing surface, the exterior panel having a first level of translucence; and
an interior panel comprising a permeable nonwoven material having barrier properties and having a first surface and a second opposing surface, the interior panel having a second level of translucence that is higher than the first level of translucence of the exterior panel, wherein the difference between the first level of translucence and the second level of translucence allows for identification of a breach, wherein the interior panel includes a plurality of bond points and the bond points define discrete locations having higher translucence than locations on the permeable nonwoven material of the interior panel that are not bond points.

2. The system of claim 1, wherein the plurality of bond points on the interior panel provide the interior panel with at least 15 percent higher translucence than locations on the permeable nonwoven material of the interior panel that are not bond points.

3. The system of claim 1, wherein the system is a steam sterilization wrap system.

4. The system of claim 1, wherein the system is an ethylene oxide sterilization wrap system.

5. The system of claim 1, wherein the exterior panel and the interior panel are a single sheet of permeable nonwoven material having barrier properties, the single sheet being folded over to form the exterior panel and the interior panel.

6. The system of claim 1, wherein the exterior panel and the interior panel are independent sheets of material.

7. The system of claim 1, wherein the exterior panel and the interior panel each have a periphery and the exterior panel and the interior panel are overlaid.

8. The system of claim 1, wherein at least one of the permeable nonwoven materials having barrier properties is a spunbond/meltblown/spunbond material.

9. The system of claim 1, wherein the difference in translucence between the second panel and the first panel is at least 45 percent.

10. The system of claim 1, wherein the difference in translucence between the second panel and the first panel is 75 percent or more.

11. The system of claim 1, wherein the difference in translucence between the second panel and the first panel is 250 percent or more.

12. The system of claim 1, wherein the difference in translucence between the second panel and the first panel is at least 15 percent.

13. A sterilization wrap system comprising: a permeable nonwoven material having barrier properties, the permeable nonwoven material including:
an exterior sheet having a first surface and a second opposing surface, the exterior sheet having a first level of translucence; and
an interior sheet having a first surface and a second opposing surface, the interior sheet having a second level of translucence that is higher than the first level of translucence of the exterior sheet, wherein the difference between the first level of translucence and the second level of translucence allows for identification of a breach on a sheet of the sterilization wrap system, wherein the interior sheet includes a plurality of bond points and the bond points define discrete locations having higher translucence than locations on the interior sheet that are not bond points.

14. The system of claim 13, wherein the plurality of bond points on the interior sheet provide the interior sheet with at least 15 percent higher translucence than locations on the interior sheet that are not bond points.

15. The system of claim 13, wherein the exterior sheet and the interior sheet are a single sheet of permeable nonwoven material having barrier properties, the single sheet being folded over to form the exterior sheet and the interior sheet.

16. The system of claim 13, wherein the exterior sheet and the interior sheet are independent sheets of material.

17. The system of claim 13, wherein the exterior sheet and the interior sheet each have a periphery and the exterior sheet and the interior sheet are overlaid.

18. The system of claim 13, wherein at least one of the exterior sheet or the interior sheet is a spunbond/meltblown/spunbond material.

19. The system of claim 13, wherein the difference in translucence between the interior sheet and the exterior sheet is at least 45 percent.

20. The system of claim 13, wherein the difference in translucence between the interior sheet and the exterior sheet is 75 percent or more.

21. The system of claim 13, wherein the difference in translucence between the interior sheet and the exterior sheet is 250 percent or more.

22. The system of claim 13, wherein the difference in translucence between the interior sheet and the exterior sheet is at least 15 percent.

* * * * *